United States Patent [19]

Smith et al.

[11] Patent Number: 4,529,693

[45] Date of Patent: Jul. 16, 1985

[54] DETECTING NEOPLASTIC MAMMARY EPITHELIAL CELLS BY DETECTING THIOESTERASE II MARKER

[75] Inventors: Stuart Smith, Lafayette, Calif.; Louis J. Libertini, Corvallis, Oreg.; Betty J. Thompson, San Francisco, Calif.

[73] Assignee: Children's Hospital Medical Center of Northern California, Oakland, Calif.

[21] Appl. No.: 560,030

[22] Filed: Dec. 9, 1983

[51] Int. Cl.³ .............. G01N 33/52; G01N 33/54; G01N 33/58

[52] U.S. Cl. .............................. 435/7; 424/3; 435/19; 436/64; 436/519; 436/813

[58] Field of Search ............ 424/3; 435/7, 19; 436/64, 519, 813

[56] References Cited

U.S. PATENT DOCUMENTS

| | | | |
|---|---|---|---|
| 4,351,823 | 9/1982 | Rubin | 435/19 X |
| 4,383,985 | 5/1983 | Bartorelli | 436/813 |
| 4,403,040 | 9/1983 | Van Aken | 436/64 X |
| 4,424,278 | 1/1984 | Bucovaz | 436/64 X |
| 4,452,904 | 6/1984 | Haagensen | 436/813 X |
| 4,461,833 | 7/1984 | Gordon | 436/813 X |
| 4,486,538 | 12/1984 | Bogoch | 436/813 X |

OTHER PUBLICATIONS

Chemical Abstracts, 100: 117478m (1984).
Libertini & Smith (1978), J. Biol. Chem., 253:1393–1401.
Smith & Ryan (1979), J. Biol. Chem., 254:8932–8936.
Stuart Smith (1980), J. Dairy Science, 63:337–352.
J. M. Nolin et al., (1982), J. Endocr., 94:251–256.
Pasco, David et al., (1982), Exp. Cell Res, 141:313–324.
L. J. Libertini et al., (1980), Biochimica et Biophysica Acta., 618:185–191.
Stuart Smith (1983), Biochem. J., 212:155–159.

Primary Examiner—Sidney Marantz
Attorney, Agent, or Firm—Townsend and Townsend

[57] ABSTRACT

Methods are provided for detecting thioesterase II enzyme in both tissue and serum samples. The presence of thioesterase II in other than mammary epithelial tissue is associated with neoplastic mammary epithelial cells.

11 Claims, No Drawings

DETECTING NEOPLASTIC MAMMARY EPITHELIAL CELLS BY DETECTING THIOESTERASE II MARKER

BACKGROUND OF THE INVENTION

1. Field of the Invention

The ability to detect and diagnose cancer through the identification of tumor markers is an area of widespread interest. Tumor markers are substances, typically proteins, glycoproteins, polysaccharides, and the like, which are produced by the tumor cells and characteristic thereof. Often, the tumor marker is produced by normal cells as well as tumor cells. In the tumor cell, however, the production has become atypical. For example, production of the tumor marker may be greatly increased in the cancer cells. In some cases, intracellular enzymes may be released into blood circulation when the cell becomes malignant. In other cases, the tumor marker remains on the cell surface and can be localized.

The identification of novel tumor markers is thus desirable for the detection and diagnosis of cancer.

2. Description of the Prior Art

A particular enzyme identified as thioesterase II has been identified in rat mammary glands. This enzyme functions in the production of medium-length fatty acids. See Libertini and Smith (1978) J. Biol. Chem. 253:1393-1401; Smith and Ryan (1979) J. Biol. Chem. 254:8932-8936; Smith (1980) J. Dairy Sci. 63:337-352; Nolin et al. (1982) J. Endocr. 94:251-256; Pasco et al. (1982) Exp. Cell Res. 141:313-324; and Smith et al. (1983) Biochim. J. 212:155-159. Cells from adenocarcinomas in rats were found to produce thioesterase II. Libertini et al. (1980) Biochimica, Biophysica, Acta. 618:185-191. Thioesterase II has not previously been identified in humans. The identification of particular tumor markers is known. See, e.g., U.S. Pat. No. 4,317,877 to Balis et al. which concerns assays for the detection of oncofoetal deoxythimidine kinase.

SUMMARY OF THE INVENTION

The present invention provides a method useful for detecting primary or metastatic breast tumors in patients suspected of having breast cancer. The method relies on the detection of a newly recognized tumor marker, thioesterase II enzyme, in serum and in tissues other than breast tissue. The presence of thioesterase II in serum is diagnostic of both primary and metastatic mammary epithelial tumors, while its presence in non-mammary tissues will indicate that neoplastic mammary epithelial cells have metastasized to that location. Detection is typically accomplished by reacting a serum or tissue sample with labelled anti-(thioesterase II) antibodies.

DESCRIPTION OF THE SPECIFIC EMBODIMENTS

Methods for detecting neoplastic mammary epithelial cells in patients suspected of having breast cancer are provided. The method comprises determining the level of thioesterase II enzyme in human tissue and/or serum samples. Screening of serum samples for elevated tioesterase II levels allows the identification of both primary mammary epithelial tumors (i.e., those breast tumors which originated in the breast) and metastatic mammary epithelial tumors (i.e., mammary epithelial tumors which metastisized from the breast to other locations). The origin of solid tumors which have metastisized from the breast may be confirmed by the presence of thioesterase II in a tissue sample from the tumor. Thioesterase II in tissue samples may be determined by conventional immunoassay or immunohistochemical techniques, employing either fixed whole cells or lysed cells. The presence of thioesterase II in serum samples can be determined by immunoassay or enzymatic assays.

Thioesterase II is an intracellular enzyme found in both normal and malignant mammary epithelial cells. The enzyme is involved in the synthesis of milk fat and is not normally found in other cells. Thus, the determination that a cell expresses thioesterase II is an indication that that cell is of mammary epithelial origin. This characteristic allows the determination of whether a solid tumor is a metastatic tumor of breast origin. In addition, since thioesterase II is not secreted by normal epithelial cells into circulation by non-lactating patients, the presence of thioesterase II in blood or lymph serum can be indicative of the presence of both primary and metastatic breast tumors.

Conveniently, the presence of thioesterase II in sample will be determined by immunoassays or histochemical staining employing antibodies reactive with human thioesterase II enzyme. Antibodies can be prepared conventionally (as described below) employing thioesterase II enzyme, or antigenic fragments thereof, as the immunogen. For example, purified human thioesterase II can be derived from a human breast cell line, such as SKBr3, Hs578T or MCF7, and pruified using affinity chromatography with anti-rat thioesterase II. Human thioesterase II is not required, and antibodies raised against thioesterase II from other vertebrates can be cross-reactive with the human enzyme. Thus, it is convenient to employ thioesterase II obtained from primates or lower order mammals, e.g. rodentia as the immunogen and to screen against partially purified human thioesterase II. Rat thioesterase II can be obtained from rat mammary epithelial cells as described by Smith (1981) Methods Enzymol. 71:188-200.

Rat thioesterase II is a monomer having molecular weight of about 33,000 and containing a single active site serine residue. The enzyme exhibits a broad pH optimum between 7.5 and 8.5 and is active against a variety of model substrates; highest activity is observed with acyl thioesters containing pantetheine or cysteamine moieties. The natural substrate for the enzyme appears to be the acyl-S-4'-phosphopantetheine-fatty acid synthetase thioester.

Once a sufficient quantity of a thioesterase II enzyme has been isolated, antibodies may be obtained by injecting the thioesterase II into a wide variety of vertebrates in accordance with conventional techniques with repeated injections in accordance with a predetermined schedule. Usually, the animals are bled periodically with successive bleeds having improved titer and specificity. The thioesterase II antigen may be injected intramuscularly, intraperitoneally, subcutaneously, or the like. Usually a vehicle is employed, such as complete or incomplete Freund's adjuvant. If desired, monoclonal antibodies can be prepared according to the now classic teachings of Kohler and Milstein (1976) Eur. J. Immunol. 6:511-519.

Once antibodies having suitable specificity have been prepared, a wide variety of immunological assay methods are available. Numerous competitive and non-competitive protein binding assays have been described in the scientific and patent literature, and a large number of such assays are commercially available. Exemplary immunoassays which are suitable for detecting the thioesterase II in a suitably prepared biological sample include those described in U.S. Pat. Nos. 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876.

It will usually be necessary to pretreat the biological sample in some manner prior to performing the immunoassay. Sample preparation will vary depending on the source of the biological sample. Solid tumors and other tissues will be prepared by fixing, embedding and sectioning by standard procedures. Serum samples will typically be prepared by clotting whole blood and isolating the supernatant in accordance with conventional techniques.

Conventional immunohistochemical staining techniques may also be used for detecting thioesterase II in tissue samples. For example, cells from the tissue sample may be fixed on a slide, typically by exposure to formalin in a buffer at physiologic pH followed by suspension in acetone and pelleting onto gelatin-coated slides by centrifugation. The thioesterase II may then be localized, either by exposure to labelled anti-(thioesterase II) or by exposure to unlabelled anti-(thioesterase II) and a labelled secondary antibody. The level of thioesterase II present is directly proportional to the amount of bound label.

As an alternative to the immunoassays, the presence of the thioesterase II enzyme can be detected directly by observing its enzymatic activity in an enzyme assay. For example, by providing labelled substrate for the enzyme, the observed turnover rate of the enzyme can be related directly to the enzyme concentration.

The following experiments are offered by way of illustration and not by way of limitation.

EXPERIMENTAL

Materials and Methods

1. Origin of Cellular Material

The following established cell lines were used in these studies: SKBr3 (Fogh and Trempe, HUMAN TUMOR CELL LINES IN VITRO (1975), Fogh, ed., Plenum Press, New York, pp. 119-159) and MCF7 (Soule et al. (1973) JNCI 51:1409-1416) derived from metastatic breast carcinomas, 578T (Hackett et al. (1977) JNCI 58:1795-1860) derived from a primary breast carcinosarcoma, H 578Bst (ibid.), a putative myoepithelial cell line derived from the same breast tissue, Hela (Gey Go et al. (1952) Cancer Res. 12:264-265) derived from a cervical carcinoma and HT29 (Fogh and Trempe, supra.) derived from a primary colon carcinoma. These cells were maintained in Dulbecco's modified Eagle's medium essential medium supplemented with 5% fetal bovine serum, 4.5 mg/ml glucose, 5 μg/ml insulin, 100 units/ml penicillin and 100 μg/ml streptomycin.

Short term cultures of human mammary epithelial cells were derived from tissue removed surgically from reduction mammoplasties, mastectomies and metastatic lesions. The tissue was processed as previously described (Stampfer et al. (1980) In vitro 16:415-425) and grown in culture in an enriched medium which supported active cell proliferation for 2-4 passages (ibid., Stampfer (1982) In vitro 18:531-537).

Milk cells were obtained by centrifugation of fresh human milk. Enrichment for epithelial cells was achieved by negative adsorption.

2. Preparation of Antibodies

Thioesterase II (Smith (1981) Meth. Enzymol. 71:188-200) and fatty acid synthetase (Smith (1981) Meth. Enzymol. 71:181-188) were isolated from lactating rat mammary gland. Purity of the enzyme preparation is routinely greater than 95%. Rabbit antibodies against thioesterase II were raised in accordance with conventional techniques and then purified by ammonium sulphate precipitation followed by affinity chromatography on sepharose-antigen columns, essentially as recommended by Pharmacia, Uppsala, Sweden. Rabbit antibodies raised against human milk-fat globule membranes (Ceriani et al. (1982) PNAS USA 74:582-586) were obtained from Dr. Roberto Ceriani of Children's Hospital, Oakland, Calif.

3. Immunohistochemical Procedures

Cells were stained for human mammary epithelial cell surface antigens by indirect immunofluorescense, using a first layer of rabbit anti-(human milk fat globule membrane) serum and a second layer of fluoresceinated goat anti-(rabbit IgG) (ibid.; Peterson et al. (1979) Int. J. Cancer 22:570-575).

For immunohistochemical staining of intracellular enzymes, cells were first fixed for several hours at 4° C. in 3% formalin/0.15M NaCl/0.01M sodium phosphate buffer (pH 7.2) and rinsed in 0.15M NaCl/0.01M sodium phosphate buffer (pH 7.2). Then the cells were suspended in acetone, pelleted onto gelatin-coated slides by centrifugation, and dried in air. Primary antibody (either rabbit anti-(human fatty acid synthetase) or rabbit anti-(rat thioesterase), diluted in 0.15M NaCl/0.01M sodium phosphate buffer (pH 7.2)/4% bovine serum albumin, was applied to the surface of the slide for 30 min. at room temperature, then removed with a pipette. The slides were rinsed for 20 min. in 0.15M NaCl/0.01M sodium phosphate buffer (pH 7.2) and then layered with the fluoresceinated goat anti-(rabbit IgG) antibodies diluted in 0.15M NaCl/0.01M sodium phosphate buffer (pH 7.2) 4% bovine serum albumin. Slides were washed free of unabsorbed antibodies as before, drained, layered with 0.15M NaCl/0.01M sodium phosphate buffer (pH 7.2)/90% glycerin and overlaid with a coverslip.

4. Assay of Enzyme Activities

Cells were homogenized and cytosols prepared as described previously (Thompson and Smith (1982) Biochem. Biophys. Acta. 712:217-220). Thioesterase II was assayed radiochemically, using $^{14}C$-fatty acyl-fatty acid synthetase as substrate (Smith et al. (1983) Biochem. J. 212:155-159). Glucose 6-phosphate dehydrogenase (Horecker and Smyrniotis (1955) Meth. Enzymol. 1:323-327), malate dehydrogenase (Ochoa (1955) Meth. Enzymol. 1:735-739), lactate dehydrogenase (Neilands (1955) Meth. Enzymol. 1:499-454) and S-acetoacetyl N-acetylcysteamine reductase (Smith et al. (1976) PNAS USA 73:1184-1188) were assayed spectrophotometrically.

5. Estimation of Chain-length of Fatty Acid Synthesis by Human Breast Cell Lines Cells were incubated with labelled substrates (Thompson and Smith (1982), supra.) and the fatty acids extracted and analyzed by gas-liquid radiochromatography (Smith et al. (1983) supra.)

6. Preparation of Immobilized Monospecific Anti-(rat)-Medium-Chain Acyl-S-Fatty Acid Synthetase Antibodies and Their Use In Detecting Immunoreactive Thioesterase in Human SKBr3 Cytosol Monospecific ("affinity-purified") antibodies to fatty acid synthetase (FAS) were coupled to Sepharose ® 4B essentially as recommended by the manufacturer (Pharmacia). About 0.3 mg of antibody was bound to 0.7 ml of Sepharose ® 4B suspension. The immobilized antibodies were equilibrated with 0.25M potassium phosphate buffer (pH 7)/1 mM dithiothreitol/1 mM EDTA and tumbled gently with SKBr3 cytosol at 4° C. At intervals the suspension was centrifuged briefly, a portion of the supernatant was removed and the remaining sample returned to the tumbling device. The extent of dilution of the cytosol, on mixing with the Sepharose ® 4B suspension, was ascertained using an isotopic tracer technique. The portions of supernatant removed at various intervals were maintained at 4° C. for the duration of the experiment and all samples were assayed for enzyme activities at the same time.

Results

1. Anti-Thioesterase II Antibodies Will Stain SKBr3 Cells

SKBr3 cells were stained for thioesterase II as set forth in section 3 of Materials and Methods. Staining was observed.

The SKBr3 cell line has been characterized as breast epithelial based on morphological considerations (Fogh and Trempe (1975), supra.). To confirm this characterization, antibodies raised against the human milk fat globule membrane were localized on the surface of the SKBr3 cells. The presence of fatty acid synthetase, a cytosolic enzyme which is present in unusually high amounts in these cells was also immunohistochemically localized.

Control reactions were performed in which the first layer antibody was omitted or replaced with nonimmune rabbit serum or replaced with anti-thioesterase antiserum which had been previously passed down an affinity column containing purified antigen bound to Sepharose ® 4B. No staining of the SKBr3 cells was observed. It was clear, therefore, that the observed immunofluorescence of the SKBr3 cells was dependent on prior exposure to anti-rat thioesterase antibodies.

2. Confirmation of the Presence of Thioesterase II in SKBr3 Cells

Thioesterase II is a key enzyme in the biosynthesis of medium chain fatty acids (Smith (1980) J. Dairy Sci. 63:337–352). Thus, if functional thioesterase II is present in the SKBr3 cells, then the cells should synthesize medium chain fatty acids. This prediction was confirmed when fatty acids of chain length $C_8$–$C_{14}$ were found to account for over 60% of fatty acid synthesized by SKBr3 cells from labelled precursors.

The presence of thioesterase II was demonstrated directly using a highly specific enzyme assay as described by Smith (1981), supra. Thioesterase II activity was measurable at a level of 0.1 nmole acyl-S-FAS per min per mg cytosolic protein.

The presence of thioesterase II was further confirmed using a depletion assay. Anti-rat thioesterase antibodies coupled to Sepharose ® were incubated with SKBr3 cytosol and the activity of a number of enzymes remaining in the liquid phase was determined. Over 75% of the thioesterase II enzyme activity was depleted from the liquid phase. The activity of the following control enzymes was unaffected: lactate dehydrogenase, malate dehydrogenase, glucose-6-phosphate dehydrogenase, and S-acetyoacetyl N-acetylcysteamine reductase.

3. Immunohistochemical Identification of Human Cells of Breast Epithelial Origin Referring to Table 1, normal epithelial cells, obtained from reduction mammoplasty surgery or from the milk of lactating mothers, stained intensely for thioesterase II (Table 1). In addition to SKBr3, two other mammary epithelial cell lines, MCF7 and Hs578T, gave positive immunohistochemical reactions for the enzyme. Cells obtained from two mammary epithelial tumors (Hs157T and 192T) from a metastatic lesion, suspected as being of breast origin and from a region of tissue surrounding a mammary tumor, all stained clearly. All of these mammary cell lines and tumors also stain positively using antibodies raised against the human milk fat globule membrane (results not shown). Three samples, Hela cells, a colon carcinoma (Ht29) and a mammary cell line (Hs578T) suspected as being of myoepithelial origin failed to give positive immunohistochemical reactions for thioesterase II.

In accordance with the subject invention, accurate and sensitive assays are provided for detecting the presence of thioesterase II enzyme in biological samples. The method is useful for detecting mammary epithelial cells, and is particularly useful for detecting neoplastic mammary epithelial cells which have metastisized from a primary breast tumor. Additionally, the presence of the thioesterase II enzyme in serum can be indicative of primary or metastatic mammary epithelial tumors.

TABLE 1

IMMUNOHISTOCHEMICAL SCREENING OF HUMAN CELLS FOR THIOESTERASE II

| Type of Cells | Code | Source | Passage Level | Immunofluorescense Score |
|---|---|---|---|---|
| Non-cultured | MC | Milk cells | — | +++ |
| Short-Term cultures | H48 | Normal reduction mammoplasty (patient aged 16 years) | 2 | ++++ |
| | H161 | Normal reduction mammoplasty (patient aged 17 years) | 2 | +++/++++ |
| | H195 | Mild fibrocystic reduction mammoplasty (patient aged 24 years) | 2 | ++/+++ |
| | H208 | Ductal ectasia, focal apocrine metaplasia, reduction mammoplasty (patient aged 45 years) | 2 | +++/++++ |
| | H157T | Lobular carcinoma (patient aged 43 years) | 2 | +++ |

TABLE 1-continued

IMMUNOHISTOCHEMICAL SCREENING OF
HUMAN CELLS FOR THIOESTERASE II

| Type of Cells | Code | Source | Passage Level | Immunofluorescense Score |
|---|---|---|---|---|
| | H192T | Lobular carcinoma (patient aged 42 years) | 1 | +++ |
| | H192P | Non-tumor tissue from H192 | 1 | ++/+++ |
| | PH303 | Metastatic breast carcinoma in vagina (patient aged 68 yrs) | 2 | ++ |
| Cell Lines | SKBr3 | Metastatic mammary adenocarcinoma | 12 | ++ |
| | MCF7 | Metastatic mammary carcinoma | 22 | ++ |
| | Hs578T | Primary mammary carcinosarcoma | 32 | +++/++++ |
| | 578Bst | Putative myoepithelial, from 578 | 11 | 0 |
| | Hela | Cervical carcinoma | nd | 0 |
| | Ht29 | Colon carcinoma | nd | 0 | nd = not determined

Although the foregoing invention has been described in some detail by way of illustration and example for purposes of clarity and understanding, it will be obvious that certain changes and modifications may be practiced within the scope of the appended claims.

What is claimed is:

1. A method for detecting neoplastic mammary epithelial cells in a patient suspected of having a cancer of breast origin, said method comprising detecting thioesterase II enzyme in a serum sample or tissue sample other than normal breast tissue.

2. A method as in claim 1, wherein the tissue sample is a solid tumor.

3. A method as in claim 2, wherein the tumor is other than a primary mammary epithelial tumor.

4. A method as in claim 1, wherein the presence of thioesterase II is determined by exposing the tissue or serum sample to labelled antibodies specific for said thioesterase II and determining the formation of specific complexes.

5. A method as in claim 1, wherein the tissue sample is fixed to a substrate and the thioesterase II is histochemically stained.

6. A method for detecting neoplastic mammary epithelial cells in a human biological sample, said method comprising combining the sample with antibodies specific for thioesterase II enzyme and determining the formation of specific complexes.

7. A method as in claim 6, wherein the antibodies are raised against rat thioesterase II enzyme.

8. A method as in claim 6, wherein the biological sample is a solid tumor.

9. A method as in claim 8, wherein the solid tumor is other than a primary mammary epithelial tumor.

10. A method as in claim 6, wherein the biological sample is a serum sample.

11. A method as in claim 8, wherein the cells of the solid tumor are fixed to a substrate and the fixed cells are histochemically stained.

* * * * *